United States Patent [19]

Campbell

[11] Patent Number: 4,539,321

[45] Date of Patent: * Sep. 3, 1985

[54] 5-DIAZA-ARYL-3-SUBSTITUTED PYRIDONE COMPOUNDS

[75] Inventor: Henry F. Campbell, Lansdale, Pa.

[73] Assignee: William H. Rorer, Inc., Fort Washington, Pa.

[ * ] Notice: The portion of the term of this patent subsequent to Apr. 30, 2002 has been disclaimed.

[21] Appl. No.: 493,336

[22] Filed: May 10, 1983

Related U.S. Application Data

[63] Continuation-in-part of Ser. No. 314,692, Oct. 26, 1981.

[51] Int. Cl.³ .................. A61K 31/495; A61K 31/505; C07D 237/00; C07D 401/00
[52] U.S. Cl. .................................... 514/252; 514/255; 514/256; 514/269; 544/239; 544/240; 544/241; 544/333; 544/360
[58] Field of Search ............... 544/333, 360, 239, 240, 544/241; 424/250, 251

[56] References Cited

U.S. PATENT DOCUMENTS 4,107,315 8/1978 Lesher et al. .................. 544/333
4,432,979 2/1984 Campbell ...................... 544/333

FOREIGN PATENT DOCUMENTS 2070606 9/1981 United Kingdom ............... 544/333

*Primary Examiner*—Donald G. Daus
*Assistant Examiner*—Cecilia Shen
*Attorney, Agent, or Firm*—James A. Nicholson; Alexis Barron; Martin F. Savitzky

[57] ABSTRACT

5-Diaza-aryl-3-substituted-2-pyridone compounds useful for increasing cardiac contractility, pharmaceutical compositions and a method for the treatment of congestive heart failure comprising the use of said compounds.

18 Claims, No Drawings

5-DIAZA-ARYL-3-SUBSTITUTED PYRIDONE COMPOUNDS

This application is a continuation-in-part application of copending Ser. No. 314,692, filed Oct. 26, 1981.

FIELD OF THE INVENTION

This invention relates to novel 5-heteroaryl-substituted-2-pyridones, useful as cardiotonic agents for the treatment of congestive heart failure, to their preparation and to pharmaceutical compositions comprised thereof.

REPORTED DEVELOPMENTS

Congestive heart failure is a life-threatening condition in which myocardial contractility is depressed so that the heart is unable to adequately pump the blood returning to it. Normal pathologic sequelae include decreased cardiac output, venous pooling, increased venous pressure, edema, increased heart size, increased myocardial wall tension, and eventually cessation of contractility. Digitalis glycosides have long been used to increase myocardial contractility and reverse the detrimental changes seen in congestive heart failure. More recently, dopamine, dobutamine, and amrinone have been used to provide necessary inotropic support for the failing heart.

Other reported inotropic drugs include the 5-pyridyl substituted pyridones, reported by Lesher and Opalka, where cardiotonic activity is exhibited when the substituents in the 3-position of the pyridones are hydrogen, cyano, amino, acetylamino, loweralkylamino, or diloweralkylamino (see U.S. Pat. Nos. 4,004,012, 4,072,746, 4,107,315, 4,137,233); when the 3-position of the pyridone is substituted by diloweralkyl amino methylene malonate (see U.S. Pat. No. 4,199,586); and when the 3-position in acylamino (see U.S. Pat. No. 4,271,168). The most preferred 5-pyridyl-pyridone, "Amrinone", 3-amino-5-(4-pyridyl)-2(1H)-pyridone, is reported to cause a 39 to 98% increase in cardiac contractile force with a duration of action of more than three hours at doses of 1.9 to 10 mg/kg, as reported in U.S. Pat. No. 4,107,315. At 10 mg/kg, however, an increase in heart rate is observed.

Bormann has reported other 3-amino substituted pyridone cardiotonics having various heterocyclic substituents in the 5-position (GB No. 2070606A; PCT published Appl. No. PCT/CH81/00023).

Lesher and Opalka have reported that 5-(4-pyridyl)-pyridones where the 3-position is halo substituted are useful intermediates for the preparation of compounds having cardiotonic properties. Pyridones wherein the 5-position is substituted by a heteroaryl group other than pyridyl and the 3-position is other than amino have not been reported to have positive inotropic activity or cardiotonic activity.

The present invention relates to a class of novel 5-heteroaryl-3-substituted pyridones which exhibit cardiotonic activity in humans and mammals and which have the advantage of producing relatively small increases in heart rate at doses producing a positive inotropic effect.

SUMMARY OF THE INVENTION

This invention relates to the novel compounds described by the structural Formula I:

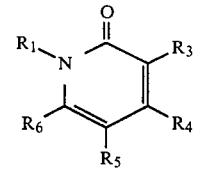

wherein:

$R_1$ is hydrogen, lower alkyl, hydroxy loweralkyl, or phenloweralkyl;

$R_3$ is lower alkyl, cyano, guanidino, thioureido, ureido, carboxyl, lower alkoxy, hydroxy, hydroxy loweralkyl, loweralkyl acylamino, carbamoyl, carbamoyl guanidino, or cyanoguanidino;

$R_4$ and $R_6$ are each independently hydrogen or lower alkyl;

$R_5$ is a 5 or 6 membered ring heteroaryl ring including two nitrogen atoms in the ring, wherein one or more of the hetero ring hydrogen atoms may be substituted by halo, lower alkyl, halo loweralkyl, hydroxy loweralkyl, hydroxy, lower alkylamino, dilower alkylamino, amino, loweralkyl acylamino, lower alkanoyl, cyano or nitro; and, the acid addition salts thereof.

This invention also relates to methods of preparing the compounds of Formula I, to pharmaceutical compositions for use in increasing cardiac contractility in humans and to the uses of these compounds in the treatment of cardiac failure in humans and other mammals.

DETAILED DESCRIPTION

Certain of the compounds of Formula I may exist in enolic or tautomeric forms, and all of these forms are considered to be included within the scope of this invention.

The compounds of this invention which have particular usefulness as cardiotonic agents are described by the Formulae II to VII.

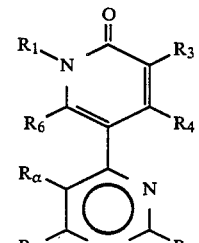 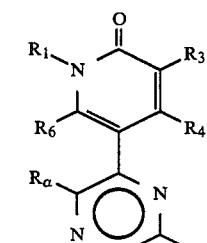

(II)   (III)

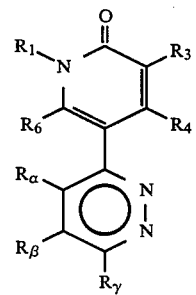 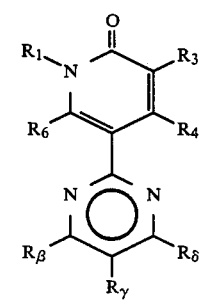

(IV)   (V)

-continued

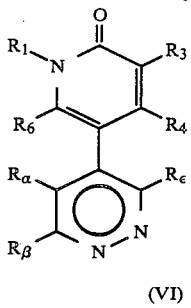

(VI)

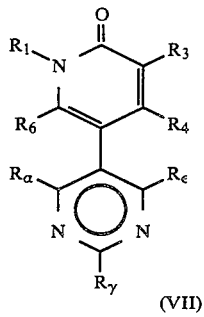

(VII)

wherein:

$R_1$, $R_3$, $R_4$ and $R_6$ are as described above, and $R_\alpha$, $R_\beta$, $R_\gamma$, $R_\delta$ and $R_\epsilon$ are each independently hydrogen, halo, lower alkyl, halo loweralkyl, hydroxy loweralkyl, hydroxy, lower alkylamino, dilower alkylamino, amino, loweralkyl acylamino, lower alkanoyl, cyano or nitro.

The more preferred compounds are those disclosed by Formulae II to VII, wherein:

$R_1$ is hydrogen, loweralkyl of $C_1$–$C_3$ carbon atoms or hydroxy loweralkyl of $C_2$–$C_3$ carbon atoms;

$R_3$ is cyano, acetylamino, carboxyl, loweralkyl, lower alkoxy, ureido or carbamoyl;

$R_4$ is hydrogen or loweralkyl of $C_1$–$C_3$ carbon atoms;

$R_6$ is hydrogen or loweralkyl of $C_1$–$C_3$ carbon atoms;

$R_\alpha$, $R_\beta$, $R_\gamma$, $R_\delta$ and $R_\epsilon$ are hydrogen or loweralkyl.

Most preferred are those compounds disclosed by Formulae II to VII, wherein:

$R_1$ is methyl, ethyl or hydroxyethyl;

$R_3$ is acetylamino or cyano;

$R_4$ is hydrogen;

$R_6$ is hydrogen, methyl or ethyl; and $R_\alpha$, $R_\beta$, $R_\gamma$, $R_\delta$ and $R_\epsilon$ are hydrogen, methyl or ethyl.

A special embodiment of the preferred compounds includes those compounds of Formula I, wherein:

$R_1$ is methyl, ethyl or hydroxyethyl;

$R_3$ is cyano;

$R_4$ is hydrogen;

$R_5$ is 4-pyrimidinyl, 2-pyrazinyl, 3-pyridazinyl, 2-pyrimidinyl or 4-pyridazinyl; and $R_6$ is methyl or ethyl.

Other embodiments include those compounds wherein:

$R_1$, $R_3$ and $R_4$ are all lower alkyl;

$R_1$, $R_4$ and $R_6$ are all hydrogen;

$R_1$, $R_4$ and $R_6$ are all lower alkyl;

$R_1$ and $R_4$ are both hydrogen;

$R_1$ and $R_4$ are both lower alkyl;

$R_4$ and $R_6$ are both lower alkyl;

$R_4$ and $R_6$ are both hydrogen; or at least one of $R_\alpha$, $R_\beta$, $R_\gamma$, $R_\delta$ and $R_\epsilon$ is other than hydrogen.

As employed above and throughout the disclosure, the following terms, unless otherwise indicated, shall be understood to have the following meanings:

"Alkyl" means a saturated aliphatic hydrocarbon which may be either straight- or branched-chained containing from about one to about 5 carbon atoms.

"Lower alkyl" means an alkyl group as above, having 1 to about 3 carbon atoms.

The term "halo" includes all four halogens; namely, fluorine, chlorine, bromine and iodine.

"Haloalkyl" refers to a loweralkyl hydrocarbon group which may be substituted by one or more halo groups, such as trifluoromethyl, trifluoroethyl, chloromethyl, etc.

"Phenloweralkyl" means a lower alkyl group in which one or more hydrogens is substituted by a phenyl group. Preferred groups are benzyl and phenethyl, etc.

"Acylamino" means an amino group substituted by an acyl radical of a lower alkanoic acid such as acetyl, propionyl, butyryl, valeryl or stearoyl.

"Hydroxy alkyl" means an alkyl group substituted by a hydroxy group. Preferred hydroxy loweralkyl groups include hydroxymethyl, 2-hydroxyethyl, 2-hydroxypropyl, or 3-hydroxypropyl.

The compounds of this invention may be useful both in the free base form and in the form of salts, and both forms are within the scope of the invention. Acid addition salts can be formed and are simply a more convenient form for use; and in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial cardiotonic properties inherent in the free base are not vitiated by side effects ascribable to the anions. In practicing the invention it is convenient to form the free base form; however, appropriate pharmaceutically acceptable salts within the scope of the invention are those derived from mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartarate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

When a base is used for salt formation, it is preferred to form the same from a sodium or potassium base such as sodium hydroxide or potassium hydroxide.

Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures.

The compounds of this invention may be prepared by one of the following synthetic routes.

The pyridone ring may be formed in essentially two steps by first reacting a heteroarylmethyl compound with an appropriate activated methylidene reagent such as a Vilsmeier reagent and thereby result in the formation of the iminium salt of the α-heteroaryl, β-enamino ketone or aldehyde. If desired, the iminium salt may be hydrolyzed to the β-enamino ketone or aldehyde for use in subsequent steps. An exemplary reaction is detailed in Scheme I.

Scheme I

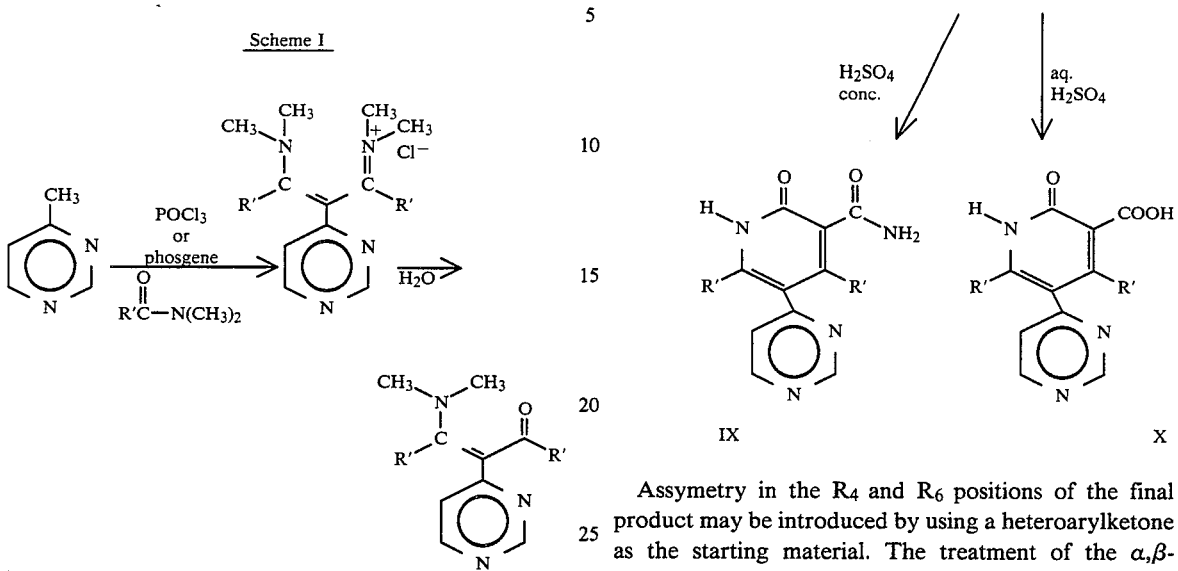

The substitution pattern in the final product is predetermined in this reaction sequence by the choice of activated methylidene reagent which ensures symmetry in the $R_4$ and $R_6$ position of the final product. The activated methylidene reagent provides the carbon units which, in this reaction sequence, form the C—$R_4$ and C—$R_6$ groups of the pyridone ring. By choosing dimethylacetamide (R'=Me), for example, both $R_4$ and $R_6$ are methyl in the final product. Treatment of the α,β-enamino carbonyl compound or the iminum salt thereof with α-cyano acetamide in the presence of base results in the 3-cyano pyridone VIII, which may be hydrolyzed to the 3-carbamoyl compound IX or the 3-carboxylic acid X. (Scheme II)

Scheme II

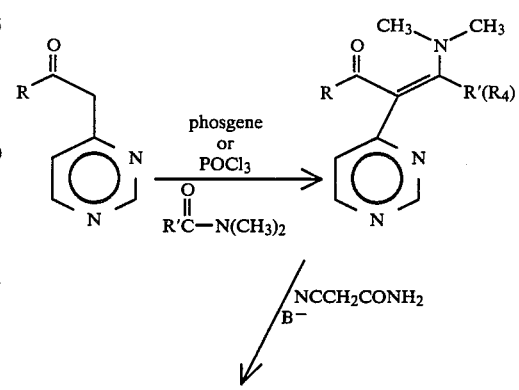

-continued
Scheme II

Assymetry in the $R_4$ and $R_6$ positions of the final product may be introduced by using a heteroarylketone as the starting material. The treatment of the α,β-enamino ketone with an appropriate nucleophile, such as α-cyanoacetamide in the presence of base, provides that R' will occupy the $R_4$ position of the pyridone. (Scheme III)

Scheme III

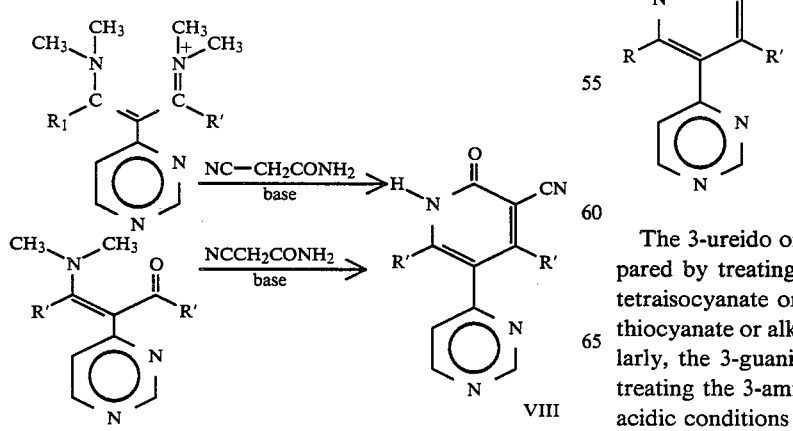

The 3-ureido or 3-thioureido compound may be prepared by treating the 3-amino compound with silicon tetraisocyanate or alkyl isocyanates or silicon tetraisothiocyanate or alkyl isothiocyanates, respectively. Similarly, the 3-guanidino compound may be prepared by treating the 3-amino compound with cyanamide under acidic conditions (Scheme IV).

Scheme IV

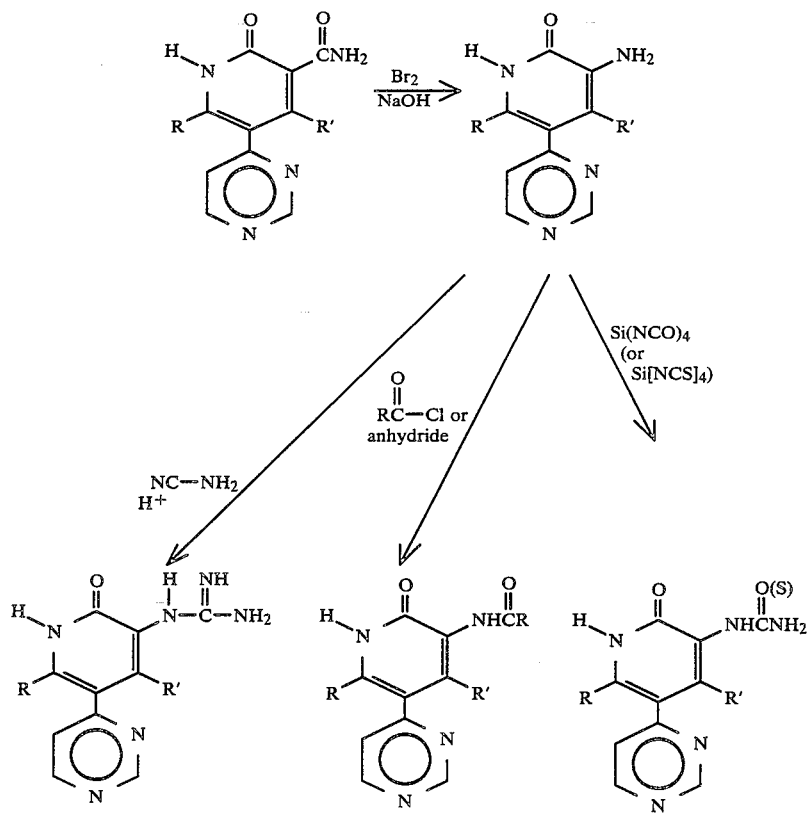

The following are illustrative examples of the preparation of the compounds of this invention and should not be construed as limitations thereof.

EXAMPLE I

Preparation of
3-Cyano-5-(4-Pyrazinyl)-2(1H)-Pyridone 16.3 g of sodium methoxide are added to a solution of 26.6 g of α-(2-pyrazinyl)-β-dimethylamino acrolein and 12.7 g of 2-cyanoacetamide in 400 ml methanol. The mixture is refluxed with stirring for 1 hour, allowed to cool and filtered. The filtered material is washed with methanol and dried yielding a slightly moist, pale green solid which is dissolved in 1250 ml of $H_2O$ and filtered. The aqueous filtrate is adjusted to pH 4–6 with 6N HCl, creating a slurry which is stirred in an ice bath for 30 minutes. The slurry is filtered and the filtered material washed with 200 ml $H_2O$, 200 ml isopropyl alcohol and 200 ml of ether to yield 3-cyano-5-(4-pyrazinyl)-2(1H)-pyridone as a beige solid, M.P. >250° C.

EXAMPLE II

The Preparation of
3-Carboxy-5-(2-Pyrazinyl)-2(1H)-Pyridone

A mixture of 25.0 g of 3-cyano-5-(2-pyrazinyl)-2(1H)-pyridone and 500 ml of 50% aqueous sulfuric acid is refluxed for 5 hours and allowed to cool. The mixture is poured onto about 1.5 kg crushed ice with mechanical stirring while cooling in an ice bath. The precipitate is collected, washed with $H_2O$, ethanol and ether and dried in vacuo overnight at 75° C. The dried solid is added to $H_2O$ and neutralized with NaOH. The neutralized solid is filtered, washed with $H_2O$, methanol and ether and recrystallized from DMF, yielding the desired 3-carboxy product as a white solid, M.P. >250° C.

EXAMPLE III

The Preparation of
3-Carbamoyl-5-(2-Pyrazinyl)-2(1H)-Pyridone 25.0 g of 3-cyano-5-(2-pyrazinyl)-2(1H-pyridone is dissolved in a solution of 228 ml concentrated sulfuric acid and 16 ml $H_2O$. The resulting dark red-orange solution is heated on a steam bath for 2 hours and then allowed to cool. The mixture is poured onto about 1.5 kg crushed ice with mechanical stirring while cooling in an ice bath, and brought to pH 5 with a solution of 342 g NaOH in 1 liter of $H_2O$. The mixture is stirred in an ice bath for 15 minutes, filtered and the solid washed with 300 ml of $H_2O$. The solid is dissolved in 1500 ml boiling dimethylformamide, filtered while hot and cooled to yield 3-carboxy-5-(2-pyrazinyl)-2(1H)-pyridone as a light beige fluffy solid.

EXAMPLE IV

The Preparation of
3-Cyano-5-(4-Pyrimidinyl)-2(1H)-Pyridone 27 g of sodium methoxide in 200 ml of methanol are added to a solution of 49.8 g of α-(4-pyrimidinyl)-β-dimethylaminoacrolein and 33.6 g of 2-cyanoacetamide in 450 l of methanol under a nitrogen atmosphere. The reaction mixture is heated to reflux for 5 minutes, cooled and filtered. The resulting solid is washed with cold methanol, ether, partially air dried, dissolved in 2 l of distilled H₂O and filtered to remove a small amount of undissolved impurity. The filtrate is acidified to a pH of 6 by addition of 6N HCl. The resultant precipitate is filtered, washed with H₂O and dried, yielding the desired 3-cyano-5-(4-pyrimidinyl)-2(1H)-pyridone as a solid, M.P.>250° C.

EXAMPLE V

The Preparation of
3-Carboxy-5-(4-Pyrimidinyl)-2(1H)-Pyridone

A solution of 23.0 g of 3-cyano-5-(4-pyrimidinyl)-2(1H)-pyridone in 300 ml of 50% aqueous $H_2SO_4$ is heated to reflux for 5 hours and allowed to cool to RT. The reaction mixture is poured onto about 1 kg of crushed ice with stirring. The resulting precipitate is filtered, washed with distilled $H_2O$, isopropanol and ether and dried in vacuo overnight. The dried solid is added to $H_2O$ and neutralized with NaOH. The resultant solid is filtered, washed with $H_2O$, methanol and ether and recrystallized from DMF, yielding the 3-carboxy pyridone as a white solid, M.P.>250° C.

EXAMPLE VI

The Preparation of
3-Carbamoyl-5-(4-Pyrimidinyl)-2(1H)-Pyridone

In a 500 ml Erlenmeyer flask, 23.0 g of 3-cyano-5-(4-pyrimidinyl)-2(1H)-pyridone is dissolved in 194.3 g of dilute $H_2SO_4$. The solution is heated on a steam bath with occasional swirling for 2½ hours. It is then poured into a slurry of 225 ml of concentrated ammonia and 610 g of ice. A white solid precipitates out and is filtered and washed with distilled $H_2O$ and then isopropanol. The white solid is dried overnight at 100° C., yielding the desired 3-carbamoyl-5-(4-pyrimidinyl)-2(1H)-pyridone.

EXAMPLE VII

The Preparation of
3-Acetamido-5-(4-Pyrimidinyl)-2-(1H)-Pyridone 2.5 ml of acetic anhydride are added to a suspension of 4.0 g of 3-amino-5-(4-pyrimidinyl)-2-(1H)-pyridone in 60 ml of pyridine. The mixture is heated on a steam bath for 2 hours and then cooled in an ice bath. The solid is filtered, washed with ethanol and dried. Recrystallization from dimethyl formamide yields the desired product, M.P.>250° C.

EXAMPLE VIII

The Preparation of
N-[5-(4-Pyrimidinyl)-2-(1H)-Pyridon-3-Yl]-N'-Methyl Thiourea Methane Sulfonate 2.0 g of methyl isothiocyanate are added to a suspension of 3.3 g of 3-amino-5-(4-pyrimidinyl)-2-(1H)-pyridone in 50 ml of pyridine. The mixture is refluxed for 3 hours, cooled in an ice bath and filtered. The filtered soild is dissolved in a boiling mixture of 50% methanol/50% dimethyl formamide and any undissolved solid filtered off. To the hot filtrate is added 3 ml of methane sulfonic acid. Cooling the solution in an ice bath causes a yellow solid to crystallize out. The solid is filtered, washed with ether and dried, yielding the methane sulfonate salt of the desired product, M.P.>250° C.

EXAMPLE IX

The Preparation of
3-Hydroxy-5-(4-Pyrimidinyl)-2-(1H)-Pyridone

A mixture of 5.0 g of 3-bromo-5-(4-pyrimidinyl)-2-(1H)-pyridone, 6.0 g of sodium methoxide and 100 ml of methanol is autoclaved at 200° for twelve hours. The solvent is distilled off in vacuo and the residue treated with water. The aqueous mixture is neutralized with acetic acid and the resulting solid collected, washed with water and dried. Recrystallization from dimethylformamide with a hot filtration yields the desired product.

EXAMPLE X

The Preparation of 3-Hydroxymethyl-5-(4-Pyrimidinyl)-2-(1H)-Pyridone

A mixture of 15 g of 5-(4-pyrimidinyl)-2-(1H)-pyridone, 200 ml of formaldehyde and 300 ml of 15% aqueous sulfuric acid is heated on a steam bath for 48 hours with additional formaldehyde (100 ml) being added every 12 hours. The reaction mixture is then cooled in an ice bath and neutralized with ammonium hydroxide. The resulting precipitate is filtered, washed with water and dried. Recrystallization from water yields the desired 3-hydroxymethyl product.

EXAMPLE XI

The Preparation of
N-[5-(4-Pyrimdinyl)-2-(1H)-Pyridon-3-Yl]-N'-Methyl Urea 3.0 ml of methyl isocyanate are added to a suspension of 4.1 g of 3-amino-5-(4-pyrimidinyl)-2-(1H)-pyridone in 100 ml of dimethyl formamide. The mixture is heated at 60° C. for 5 hours with a dry ice/acetone condenser to condense methylisocyanate. The reaction mixture is cooled in an ice bath and solid filtered, washed with ethanol and dried. The solid is recrystallized from dimethylformamide with any insoluble solid filtered off in a hot gravity filtration. On cooling the dimethylformamide solution, the desired product is obtained.

EXAMPLE XII

The Preparation of
5-(4-Pyrimidinyl)-2-(1H)-Pyridon-3-Yl Guanidine 5.0 g of 3-amino-5-(4-pyrimidinyl)-2-(1H)-pyridone are dissolved in a minimum amount of 1N hydrochloric acid and then diluted to 250 ml by addition of ethanol. To this solution are added 2.4 g of cyanamide and the mixture is refluxed for 2 hours. After cooling in an ice bath, the reaction mixture is made slighty basic by addition of dilute ammonium hydroxide. Solid which precipitates out is filtered and then recrystallized from dimethyl formamide to give the desired product.

EXAMPLE XIII

The Preparation of
1-[5-(4-Pyrimidinyl)-2-(1H)-Pyridon-3-Yl]-3-Cyanoguanidine 5.0 g of 3-amino-5-(4-pyrimidinyl)-2-(1H)-pyridone are dissolved in a minimum amount of 1N hydrochloric acid and then diluted to 250 ml by addition of ethanol. To this solution are added 6.0 g of sodium dicyanamide and the mixture is refluxed for 2 hours. After cooling in an ice bath the reaction mixture is made slightly basic by addition of dilute ammonium hydroxide. Solid which precipitates out is filtered and then recrystallized from dimethyl formamide to give the desired product.

EXAMPLE XIV

The Preparation of 1-[5-(4-Pyrimidinyl)-2-(1H)-Pyridon-3-Yl]-3-Carbamoylguanidine 4.0 g of 1-[5-(4-pyrimidinyl)-2-(1H)-pyridon-3-yl]-3-cyanoguanidine are dissolved in 50% aqueous sulfuric acid and refluxed for 3 hours. After cooling in an ice bath the reaction mixture is poured slowly into a mixture of ice and conc. ammonium hydroxide. The solid which precipitates out is filtered, resuspended in distilled water, and refiltered. Recrystallization from dimethyl formamide gives the desired product.

EXAMPLE XV

The Preparation of 3-Methyl-(4-Pyrimidinyl)-2-(1H)-Pyridone 5.3 g (0.02 mole) of 3-bromomethyl-5-(4-pyrimidinyl)-2-(1H)-pyridone (prepared from 3-hydroxymethyl-5-(4-pyrimidinyl)-2-(1H)-pyridone using $PBr_3/CHCl_3$) dissolved in 50 ml of dry DMSO is added to a flask containing 1.5 g (0.04 mole) of sodium borohydride in 50 ml of dry DMSO. The reaction mixture is stirred at RT for 2 hours. The reaction mixture is diluted with water with cooling and the resulting precipitate is filtered, washed with water and dried to yield the desired product.

The following list of compounds may be prepared according to the above-described reaction sequences and using analogous reaction conditions and starting materials, which are either commercially available or prepared by methods known to those skilled in the art.

TABLE A 3-cyano-6-methyl-5-(2-pyrimidinyl)-2(1H)-pyridone
3-cyano-6-methyl-5-(4-pyrimidinyl)-2(1H)-pyridone
3-cyano-6-ethyl-5-(3-pyridazinyl)-2(1H)-pyridone
3-cyano-6-ethyl-5-(4-pyridazinyl)-2(1H)-pyridone
3-cyano-6-ethyl-5-(2-pyrazinyl)-2(1H)-pyridone
3-carboxy-6-methyl-5-(2-pyrimidinyl)-2(1H)-pyridone
3-carboxy-6-methyl-5-(4-pyrimidinyl)-2(1H)-pyridone
3-carboxy-6-ethyl-5-(3-pyridazinyl)-2(1H)-pyridone
3-carboxy-6-ethyl-5-(4-pyridazinyl)-2(1H)-pyridone
3-carboxy-6-ethyl-5-(2-pyrazinyl)-2(1H)-pyridone
3-acetylamino-6-methyl-5-(2-pyrimidinyl)-2(1H)-pyridone
3-acetylamino-6-methyl-5-(4-pyrimidinyl)-2(1H)-pyridone
3-acetylamino-6-ethyl-5-(3-pyridazinyl)-2(1H)-pyridone
3-acetylamino-6-ethyl-5-(4-pyridazinyl)-2(1H)-pyridone
3-acetylamino-6-ethyl-5-(2-pyrazinyl)-2(1H)-pyridone
3-cyano-1,6-dimethyl-5-(2-pyrimidinyl)-2-pyridone
3-cyano-1-ethyl-6-methyl-5-(4-pyrimidinyl)-2-pyridone
3-cyano-1,6-diethyl-5-(3-pyridazinyl)-2-pyridone
3-cyano-6-ethyl-1-methyl-5-(4-pyridazinyl)-2-pyridone
3-cyano-1,6-diethyl-5-(2-pyrazinyl)-2-pyridone
3-carbamoyl-1,6-dimethyl-5-(2-pyrimidinyl)-2-pyridone
3-carbamoyl-1-ethyl-6-methyl-5-(4-pyrimidinyl)-2-pyridone
3-carbamoyl-1,6-diethyl-5-(3-pyridazinyl)-2-pyridone
3-carbamoyl-6-ethyl-1-methyl-5-(4-pyridazinyl)-2-pyridone
1,6-diethyl-3-carbamoyl-5-(2-pyrazinyl)-2-pyridone
3-acetylamino-1,6-dimethyl-5-(2-pyrimidinyl)-2-pyridone
3-acetylamino-1-ethyl-6-methyl-5-(4-pyrimidinyl)-2-pyridone
3-acetylamino-1,6-diethyl-5-(3-pyridazinyl)-2-pyridone
3-acetylamino-6-ethyl-1-methyl-5-(4-pyridazinyl)-2-pyridone
3-acetylamino-1,6-diethyl-5-(2-pyrazinyl)-2-pyridone
3-cyano-4,6-dimethyl-5-(2-pyrimidinyl)-2(1H)-pyridone
3-cyano-4-ethyl-6-methyl-5-(4-pyrimidinyl)-2(1H)-pyridone
3-cyano-4,6-diethyl-5-(3-pyridazinyl)-2(1H)-pyridone
3-cyano-6-ethyl-4-methyl-5-(4-pyridazinyl)-2(1H)-pyridone
3-cyano-4,6-diethyl-5-(2-pyrazinyl)-2(1H)-pyridone
3-ureido-4,6-dimethyl-5-(2-pyrimidinyl)-2(1H)-pyridone
3-ureido-4-ethyl-6-methyl-5-(4-pyrimidinyl)-2(1H)-pyridone
4,6-diethyl-3-ureido-5-(3-pyridazinyl)-2(1H)-pyridone
3-ureido-6-ethyl-4-methyl-5-(4-pyridazinyl)-2(1H)-pyridone
4,6-diethyl-3-ureido-5-(2-pyrazinyl)-2(1H)-pyridone
3-acetylamino-4,6-dimethyl-5-(2-pyrimidinyl)-2(1H)-pyridone
3-acetylamino-4-ethyl-6-methyl-5-(4-pyrimidinyl)-2(1H)-pyridone
3-acetylamino-4,6-diethyl-5-(3-pyridazinyl)-2(1H)-pyridone
3-acetylamino-6-ethyl-4-methyl-5-(4-pyridazinyl)-2(1H)-pyridone
3-acetylamino-4,6-diethyl-5-(2-pyrazinyl)-2(1H)-pyridone
3-cyano-1,4,6-trimethyl-5-(2-pyrimidinyl)-2-pyridone
3-cyano-1,4-diethyl-6-ethyl-5-(4-pyrimidinyl)-2-pyridone
3-cyano-1,4,6-triethyl-5-(3-pyridazinyl)-2-pyridone
3-cyano-1,4-dimethyl-6-ethyl-5-(4-pyridazinyl)-2-pyridone
3-cyano-1,4,6-triethyl-5-(2-pyrazinyl)-2-pyridone
3-carboxy-1,4,6-trimethyl-5-(2-pyrimidinyl)-2-pyridone
3-carboxy-1,4-diethyl-6-ethyl-5-(4-pyrimidinyl)-2-pyridone
3-carboxy-1,4,6-triethyl-5-(3-pyridazinyl)-2-pyridone
3-carboxy-1,4-dimethyl-6-ethyl-5-(4-pyridazinyl)-2-pyridone
3-carboxy-1,4,6-triethyl-5-(2-pyrazinyl)-2-pyridone
3-acetylamino-1,4,6-trimethyl-5-(2-pyrimidinyl)-2-pyridone
3-acetylamino-1,4-diethyl-6-methyl-5-(4-pyrimidinyl)-2-pyridone
3-acetylamino-1,4,6-triethyl-5-(3-pyridazinyl)-2-pyridone
3-acetylamino-1,4-diethyl-6-ethyl-5-(4-pyridazinyl)-2-pyridone
3-acetylamino-1,4,6-triethyl-5-(2-pyrazinyl)-2pyridone The compounds of Formula I possess positive inotropic activity and are useful as cardiotonic agents in the treatment of humans and other mammal for cardiac disorders including congestive heart failure. The effectiveness of the compounds of this invention as inotropic agents may be determined by the following pharmacologic tests which evaluate the change in cardiac contractile force upon exposure to a dose of said compounds. The anesthetized dog procedure is a standard test procedure; the inotropic results of this procedure generally correlate with the inotropic activity found in human patients.

ANESTHETIZED DOG PROCEDURE

Male mongrel dogs are anesthetized with pentobarbital (35 mg/kg i.v.) and intubated. Femoral artery and veins are cannulated for measurement of blood pressure and injection of compounds, respectively. A catheter connected to a Statham transducer is inserted into the left ventricle via the right carotid artery for measurement of left ventricular pressure, left ventricular end diastatic pressure and dP/dt. Lead II ECG and heart rate are also monitored. All parameters are measured on a Beckman Dynagraph.

The results of the anesthetized dog test show that the compounds of this invention exhibit positive inotropic activity and show dose related increases in contractile force with relatively small increases in heart rate.

A second test procedure which has been found to be an efficient means for ascertaining the inotropic activity of the compounds of this invention is described below.

GUINEA PIG ATRIA INOTROPIC SCREENING AT LOW CALCIUM CONCENTRATIONS

Guinea pigs are stunned by a sudden blow to the head; their chests are opened and hearts excised and placed in Kreb's medium (concentrations, mM: NaCl, 118.39; KCl, 4.70; $MgSO_4$, 1.18; $KH_2PO_4$, 1.18; $NaHCO_3$, 25.00; glucose, 11.66; and $CaCl_2$, 1.25) gassed with a mixture of 95% $O_2$-5% $CO_2$. Left atria are removed and inserted into warmed (33° C.) double jacketed tissue chambers containing oxygenated Kreb's medium (as above). The upper end of each tissue is attached to a Statham Universal Transducing Cell via a Statham Microscale Accessory. Resting tension on each tissue is set at 1 g and adjusted periodically.

Massive field stimulation is achieved via a pair of platinum or silver electrodes placed on opposite sides of the tissue. Electrodes are made from 20-gauge silver wire wound into a tight coil approximately 12–14 mm in diameter. Electrodes are connected to a Grass stimulator via a Grass constant current unit. Tissues are driven at 90 pulses per minute with a 5 msec duration at current levels 20% greater than threshold for continuous beat.

Cumulative concentrations of test drugs are added to the tissue bath at intervals sufficient to allow developed tension to peak at a new level.

The increase in developed tension in each tissue for each compound concentration is measured, and the results are averaged and used to construct cumulative concentration-response curves. Slopes for these regressions are calculated via the method of Finney (1971) and compared using Student's t-test.

The compoundss of this invention can be normally administered orally or parenterally, in the treatment of cardiac disorders such as heart failure in humans or other mammals.

The compounds of this invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqeuous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of inotropic active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, are also useful for intravenous injection purposes, provided that their pH is properly adjusted, suitably buffered, made isotonic with sufficient saline or glucose and sterilized by heating or by microfiltration.

The dosage regimen in carrying out the methods of this invention is that which insures maximum therapeutic response until improvement is obtained and thereafter the minimum effective level which gives relief. Thus, in general, the dosages are those that are therapeutically effective in increasing the contractile force of the heart or in the treatment of cardiac failure. In general, the oral dose may be betweeen about 0.01 mg/kg and about 50 mg/kg (preferably in the range of 0.1 to 10 mg/kg), and the i.v. dose about 0.005 to about 30 mg/kg (preferably in the range of 0.01 to 3 mg/kg), bearing in mind, of course, that in selecting the appropriate dosage in any specific case, consideration must be given to the patient's weight, general health, age, and other factors which may influence response to the drug. The drug may be administered orally 1 to 4 times per day, preferably twice daily.

I claim:

1. A compound according to the formula

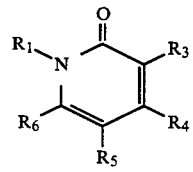

wherein:

$R_1$ is hydrogen, lower alkyl, hydroxyloweralkyl or phenloweralkyl;

$R_3$ is lower alkyl, cyano, guanidino, thioureido, ureido, carboxyl, lower alkoxy, hydroxyl, hydroxy loweralkyl, loweralkyl acylamino, carbamoyl, carbamoyl guanidino, or cyanoguanidino;

$R_4$ and $R_6$ are each independently hydrogen or lower alkyl;

$R_5$ is a 6 membered ring heteroaryl group including at least two nitrogen atoms and four carbon atoms in the ring; and, wherein:

one of the heteroaryl hydrogen atoms may be substituted by halo, lower alkyl, halo loweralkyl, hydroxy loweralkyl, hydroxy, lower alkylamino, di-lower alkylamino, amino, loweralkyl acylamino, lower alkanoyl, cyano or nitro; or a pharmaceutically acceptable salt thereof.

2. A compound according to claim 1, wherein: $R_5$ is

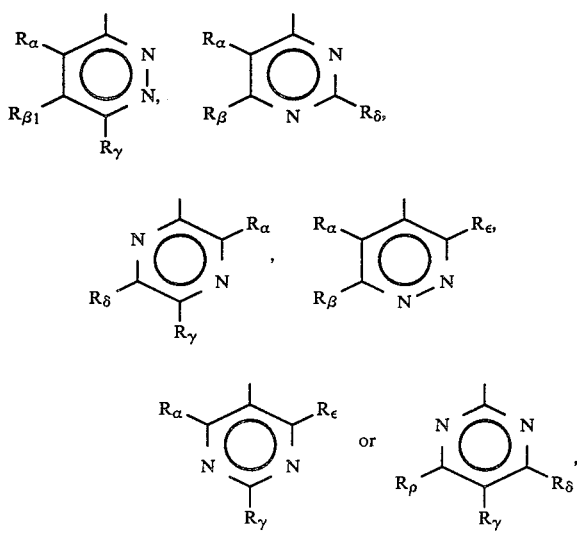

and wherein: $R_\alpha$, $R_\beta$, $R_\gamma$, $R_\delta$, and $R_\epsilon$ are each independently hydrogen, halo, lower alkyl, halo loweralkyl, hydroxy loweralkyl, hydroxy, lower alkylamino, dilower alkylamino, amino, loweralkyl acylamino, lower alkanoyl, cyano or nitro, provided that only one of $R_\alpha$, $R_\beta$, $R_\gamma$, $R_\delta$ and $R_\epsilon$ is other than hydrogen.

3. A compound according to claim 2, wherein:
$R_1$ is methyl, ethyl or 2-hydroxyethyl;
$R_3$ is acetylamino or cyano;
$R_4$ and $R_6$ are hydrogen, methyl or ethyl; and one of $R_\alpha$, $R_\beta$, $R_\gamma$, $R_\delta$ and $R_\epsilon$ is methyl or ethyl.

4. A compound according to claim 3, wherein:
$R_4$ is hydrogen; and
$R_6$ is methyl or ethyl.

5. A compound according to claim 3, wherein $R_4$ and $R_6$ are methyl or ethyl.

6. A compound according to the formula

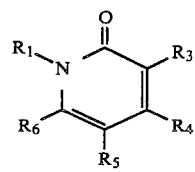

wherein:
$R_1$ is lower alkyl;
$R_3$ is cyano;
$R_4$ and $R_6$ are hydrogen or loweralkyl;
$R_5$ is pyrazinyl, pyrimidinyl, pyridazinyl, or pyrazinyl, pyrimidinyl or pyridazinyl subsituted in one position by lower alkyl, halo, haloloweralkyl, hydroxyloweralkyl, hydroxy, loweralkylamino, diloweralkylamino, amino, loweralkylacylamino, lower alkanoyl, cyano, or nitro; or a pharmaceutically acceptable salt thereof.

7. A compound according to claim 6 wherein $R_4$ and $R_6$ are lower alkyl.

8. A compound according to claim 6, wherein $R_5$ is pyrazinyl, pyrimidinyl or pyridazinyl substituted in one position by lower alkyl.

9. A compound according to claim 6, wherein $R_5$ is substituted or unsubstituted 2-pyrimidinyl or 4-pyrimidinyl.

10. A compound according to claim 1 which is 3-carboxy-5-(4-pyrimidinyl)-2(1H)-pyridone or a non-toxic salt thereof.

11. A compound according to claim 1 which is 3-carboxy-5-(2-pyrazinyl)-2-(2H)-pyridone or a non-toxic salt thereof.

12. A compound according to claim 1 which is 3-cyano-5-(4-pyrimidinyl)-2(1H)-pyridone or a non-toxic salt thereof.

13. A compound according to claim 1 which is 3-carbamoyl-5-(4-pyrimidinyl)-2(1H)-pyridone or a non-toxic salt thereof.

14. A compound according to claim 1 which is 3-cyano-5-(2-pyrazinyl)-2(1H)-pyridone or a non-toxic salt thereof.

15. A compound according to claim 1 which is 3-carbamoyl-5-(2-pyrazinyl)-2(1H)-pyridone or a non-toxic salt thereof.

16. A method for increasing cardiac contractility in a human or other mammal which comprises administering thereto an effective cardiotonic amount of a compound according to claim 1.

17. A method for the treatment of congestive heart failure in a human or other mammal comprising administering to a human or other mammal in need of such treatment an effective cardiotonic amount of a compound according claim 1.

18. A cardiotonic composition comprising an effective cardiotonic amount of a compound according to claim 1 and a pharmaceutically acceptable carrier.

* * * * *